(12) United States Patent
Wetzel et al.

(10) Patent No.: US 11,564,814 B1
(45) Date of Patent: Jan. 31, 2023

(54) PROSTHESIS COVER AND METHOD OF MANUFACTURE

(71) Applicant: Cole Designs, LLC, Iowa City, IA (US)

(72) Inventors: James Wetzel, Iowa City, IA (US); Erica Cole, Iowa City, IA (US)

(73) Assignee: James Wetzel, Iowa City, IA (US)

( * ) Notice: Subject to any disclaimer, the term of this patent is extended or adjusted under 35 U.S.C. 154(b) by 398 days.

(21) Appl. No.: 16/595,955

(22) Filed: Oct. 8, 2019

(51) Int. Cl.
| | | |
|---|---|---|
| *A61F 2/50* | (2006.01) | |
| *A61F 2/78* | (2006.01) | |
| *A61F 2/64* | (2006.01) | |
| *B33Y 50/00* | (2015.01) | |
| *B33Y 80/00* | (2015.01) | |
| *B33Y 10/00* | (2015.01) | |

(52) U.S. Cl.
CPC .......... *A61F 2/50* (2013.01); *A61F 2/64* (2013.01); *A61F 2/78* (2013.01); *B33Y 50/00* (2014.12); *B33Y 80/00* (2014.12); *A61F 2002/5001* (2013.01); *A61F 2002/505* (2013.01); *A61F 2002/5056* (2013.01); *B33Y 10/00* (2014.12)

(58) Field of Classification Search
CPC .............................................. A61F 2002/5001
See application file for complete search history.

(56) References Cited

U.S. PATENT DOCUMENTS

| | | | | |
|---|---|---|---|---|
| 4,128,903 A | * | 12/1978 | Marsh ............... | A61F 2/80 623/36 |
| 4,872,879 A | * | 10/1989 | Shamp ............... | A61F 2/80 623/36 |
| 5,108,455 A | * | 4/1992 | Telikicherla ......... | A61F 2/7812 623/36 |
| 5,133,752 A | * | 7/1992 | Mandelkern ......... | A61F 2/50 623/7 |
| 5,376,127 A | | 12/1994 | Swanson | |
| 5,507,722 A | * | 4/1996 | Richardson ......... | A61F 2/7812 602/61 |
| 5,529,575 A | * | 6/1996 | Klotz ............... | A61F 2/80 623/33 |
| 5,571,206 A | * | 11/1996 | Varn ............... | A61F 5/0125 602/26 |
| 5,571,209 A | * | 11/1996 | Brown, Sr. ......... | A61F 2/80 623/36 |
| 5,651,792 A | * | 7/1997 | Telikicherla ......... | A61F 2/7812 623/36 |
| 5,653,766 A | * | 8/1997 | Naser ............... | A61F 2/80 623/32 |
| 5,728,167 A | * | 3/1998 | Lohmann ............ | A61F 2/7812 623/36 |
| 5,880,964 A | | 3/1999 | Schall et al. | |

(Continued)

*Primary Examiner* — Jacqueline Woznicki
(74) *Attorney, Agent, or Firm* — Shuttleworth & Ingersoll, PLC; Jason Sytsma

(57) ABSTRACT

A sleeve generally shaped as a limb and an overlapping area of curvature formed in the sleeve extending a length of the sleeve. A clasp is formed from slicing the overlapping area of curvature the length of the sleeve along a line substantially perpendicular to a transverse plane to create a first end and a second end. The sleeve is openable to separate the first end and the second end of the clasp for fitting the sleeve around the prosthesis and latchable by fitting the first end of the clasp over the second end of the clasp.

15 Claims, 9 Drawing Sheets

(56) References Cited

U.S. PATENT DOCUMENTS

| | | | | |
|---|---|---|---|---|
| 5,916,190 | A * | 6/1999 | Davis, Jr. | A61F 13/06 |
| | | | | 602/61 |
| 6,669,736 | B2 | 12/2003 | Slemker et al. | |
| 6,911,049 | B2 | 6/2005 | Laghi | |
| 8,764,689 | B2 * | 7/2014 | Toth | A61H 11/00 |
| | | | | 601/134 |
| 8,801,645 | B2 * | 8/2014 | Lipshaw | A61F 13/085 |
| | | | | 450/101 |
| 9,642,766 | B2 * | 5/2017 | Lipshaw | A61F 13/10 |
| 9,707,132 | B2 * | 7/2017 | Richardson | A61H 1/008 |
| 10,117,784 | B2 * | 11/2018 | Lipshaw | A61F 13/085 |
| 10,820,648 | B2 * | 11/2020 | Hoffman | A61F 13/085 |
| 11,051,987 | B2 * | 7/2021 | Hoffman | A61F 13/00059 |
| 11,224,525 | B2 * | 1/2022 | Radspieler | A61F 2/7812 |
| 11,273,080 | B2 * | 3/2022 | Ganzoni | A61F 13/085 |
| 2006/0173553 | A1 * | 8/2006 | Holzer | A61F 2/602 |
| | | | | 623/32 |
| 2007/0150069 | A1 * | 6/2007 | Takami | A61F 2/60 |
| | | | | 623/27 |
| 2012/0095570 | A1 * | 4/2012 | Marquette | A61F 2/50 |
| | | | | 623/27 |
| 2015/0148724 | A1 * | 5/2015 | Bedard | A61L 27/44 |
| | | | | 428/339 |
| 2016/0095723 | A1 * | 4/2016 | Devito | A61F 2/78 |
| | | | | 623/27 |
| 2016/0331558 | A1 * | 11/2016 | Kampas | A61F 2/50 |
| 2019/0366639 | A1 * | 12/2019 | Barocio | B29C 64/118 |
| 2019/0387823 | A1 * | 12/2019 | O'Brien | A41B 7/02 |
| 2021/0000620 | A1 * | 1/2021 | Radspieler | A61F 2/50 |

* cited by examiner

PROSTHESIS COVER AND METHOD OF MANUFACTURE

TECHNICAL FIELD

The present invention involves a prosthesis limb cosmetic cover and method for fabricating a prosthesis limb cosmetic cover, and more particularly to a prosthesis limb cosmetic cover and method for fabricating the cosmetic cover as a unitary structure with a three-dimensional printer.

BACKGROUND INFORMATION

A prosthesis is often used to replace an amputated portion of the limb and to help restore the amputee's ability to use that limb. A prosthesis for a lower extremity amputation will often include artificial foot and ankle components coupled to an upright assembly, which is in turn coupled to a custom-fitted socket assembly. If the amputation is an above the knee, the upright assembly will often include an artificial knee joint.

Often times, a cosmetic cover is fabricated to cover the endoskeletal components of the prosthetic limb described above to simulate the outward appearance of a limb. One technique for hiding, covering, shielding or masking the structural component contemplates prosthesis foam shaped to substantially conform to the shape of a limb. Typically, the sound limb of an amputee is used as a model. The foam that covers the pylon is sculpted to look like the sound limb in shape and size. This process is expensive and time consuming.

Other types of prosthetic covers require multiple hand-crafted pieces to simulate the contour/appearance of an actual limb. Usually the resulting product is less than satisfactory because it lacks durability, is heavy and requires much more labor to install.

Accordingly, there is a need for a prosthetic cover that is durable, easy to install, and inexpensive and replicable to accommodate different aesthetics.

SUMMARY

In accordance with one aspect of the present invention, a prosthesis cover is disclosed. The prosthesis cover comprises of a sleeve generally shaped as a limb and an overlapping area of curvature formed in the sleeve extending a length of the sleeve. A clasp is formed from slicing the overlapping area of curvature the length of the sleeve along a line substantially perpendicular to a transverse plane to create a first end and a second end. The sleeve is openable to separate the first end and the second end of the clasp for fitting the sleeve around the prosthesis and latchable by fitting the first end of the clasp over the second end of the clasp.

The overlapping area of curvature in the sleeve of the prosthesis cover can be a generally s-shaped curve. The overlapping area of curvature can also be intersected by a vertically oriented plane that is perpendicular to a transverse plane at at least four times when the vertically oriented plane extends through the overlapping area of curvature in the prosthesis cover. The sleeve can be made from a thermoplastic material.

The sleeve is also formed of a single piece of material printed by a 3D printing system in one continuous and uninterrupted motion in a spirally upward motion. The method for constructing the prosthesis cover can comprise providing a digital file of a prosthesis cover; sending the digital file to a 3D printing system; and printing in a continuous motion a prosthesis cover based on the digital file. The method can include adjusting the digital file based on at least one dimension, including adjusting the digital file based on at least the following dimensions major knee, minor knee, top section, total height, major ankle and minor ankle. It is highly advantageous to form the overlapping area of curvature in the prosthesis cover while printing in the continuous motion. Afterwards, the method includes slicing the overlapping area of curvature in the prosthesis cover along a line substantially perpendicular to the transverse plane the length of the prosthesis cover for forming a clasp from the overlapping area of curvature in the prosthesis cover.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

Figure 1:
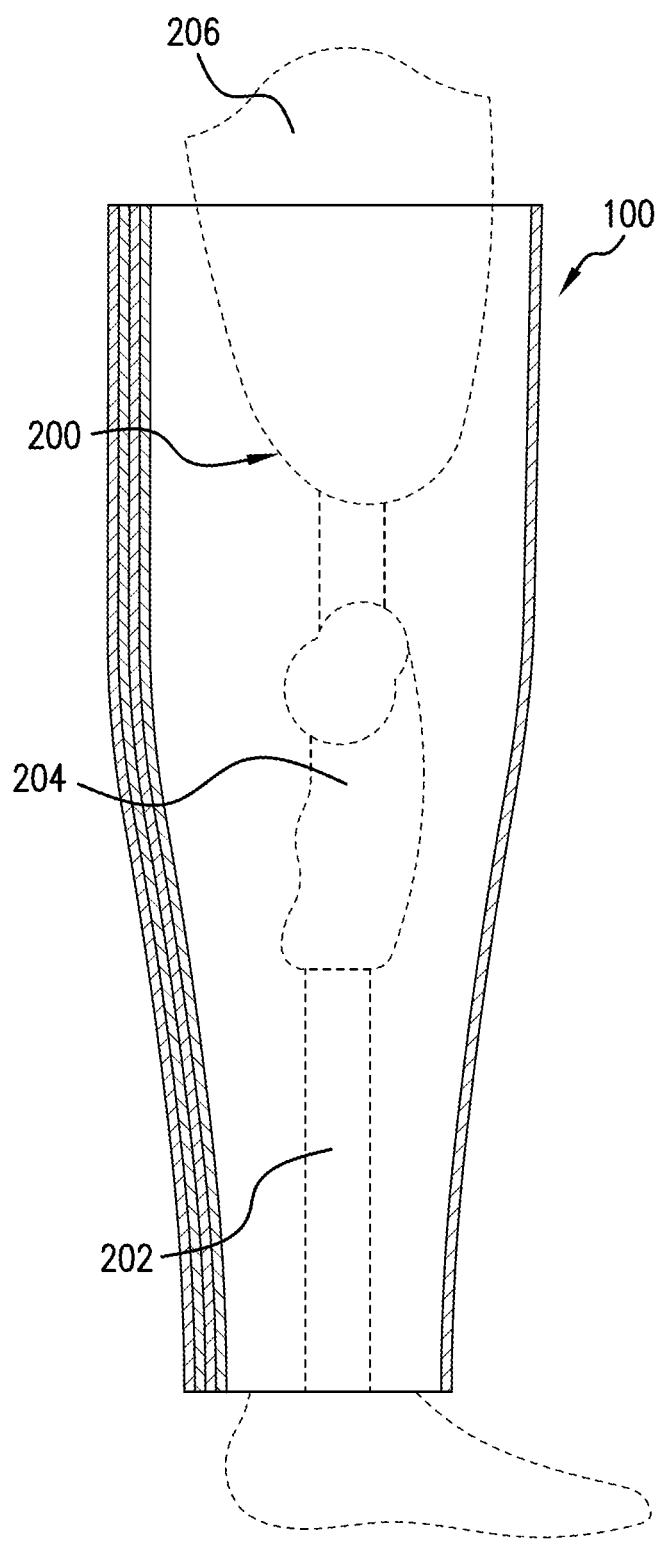
FIG. 1 is a schematic view of a cosmetic prosthesis cover in the fitted state.

Referring to FIG. 1, a prosthesis cover 100 is illustrated in a fitted state on a prosthesis 200 which is configured as a prosthetic leg. The prosthesis 200 has a distal component 202 in the form of a lower-leg tube having a prosthetic foot fastened thereon, a prosthetic knee joint 204 and a proximal prosthetic component 206 in the form of a socket. The proximal component 206 is connected in an articulated manner to the distal component 202 via the prosthetic knee joint 204.

FIGS. 2-7 shows prosthesis cover 100 from FIG. 1 in more detail. Prosthesis cover 100 comprises of a sleeve 102 generally shaped as the portion of a leg below the knee. Sleeve 102 can be tailored to each individual with dimensions B-G shown in FIG. 2. Dimension B is referred to as the major knee dimension, which is the length from the front of the knee cap to the back of the knee. Dimension C is the minor knee dimension, which is the length ninety degrees from the major knee dimension. Dimension D is the top section. Dimension E is the total height, which is the longitudinal length of the sleeve. Dimension F is the major ankle dimension, which is the dimension from the front of the foot ninety degrees from the ankle to the back side of the foot. Dimension G is the minor ankle, which is the dimension ninety degrees from the major ankle. With these dimensions B-G, sleeve 102 can be individually formed uniquely for each individual.

Prosthesis cover 100 also includes an overlapping area of curvature 104 formed in sleeve 102 that extend the total height of sleeve 102 (represented by dimension E). Overlapping area of curvature 104 is a simple and smooth curved area that doubles back on itself for forming an integrated clasp 106. Overlapping area of curvature 104 can be a generally s-shaped curve or any other shaped curve provided that overlapping area of curvature 104 has an overlapping portion. In one embodiment, prosthesis cover 100 is intersected by a vertically oriented plane 107 that is perpendicular to a transverse plane 103 at at least four points 105a, 105b, 105c, and 105d when such vertically oriented plane 107 extends through overlapping area of curvature 104.

Figure 7:
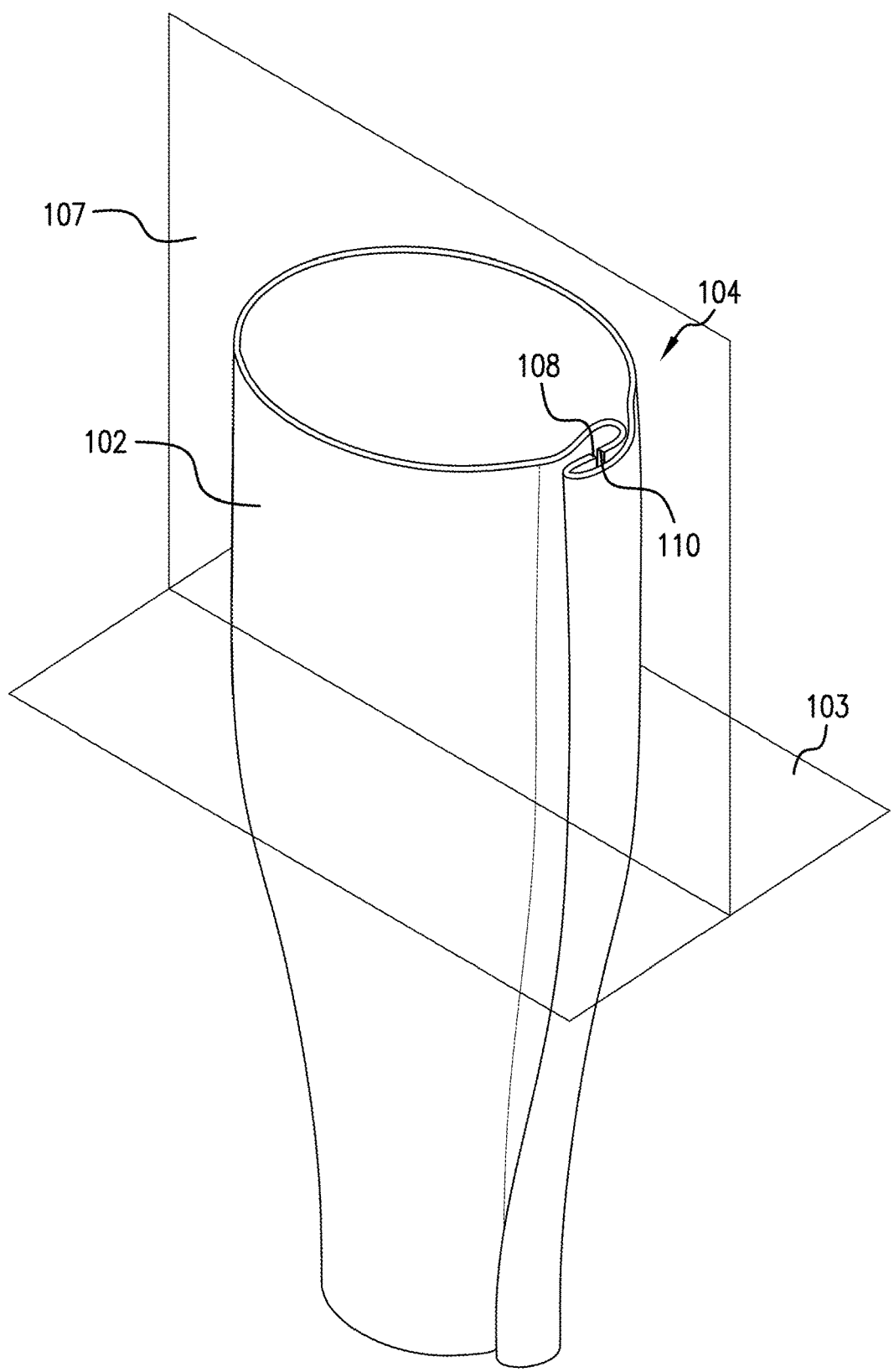
FIG. 7 shows the cosmetic cover of FIG. 1 sliced vertically about a vertically oriented plane shown in FIG. 2.
Figure 8:
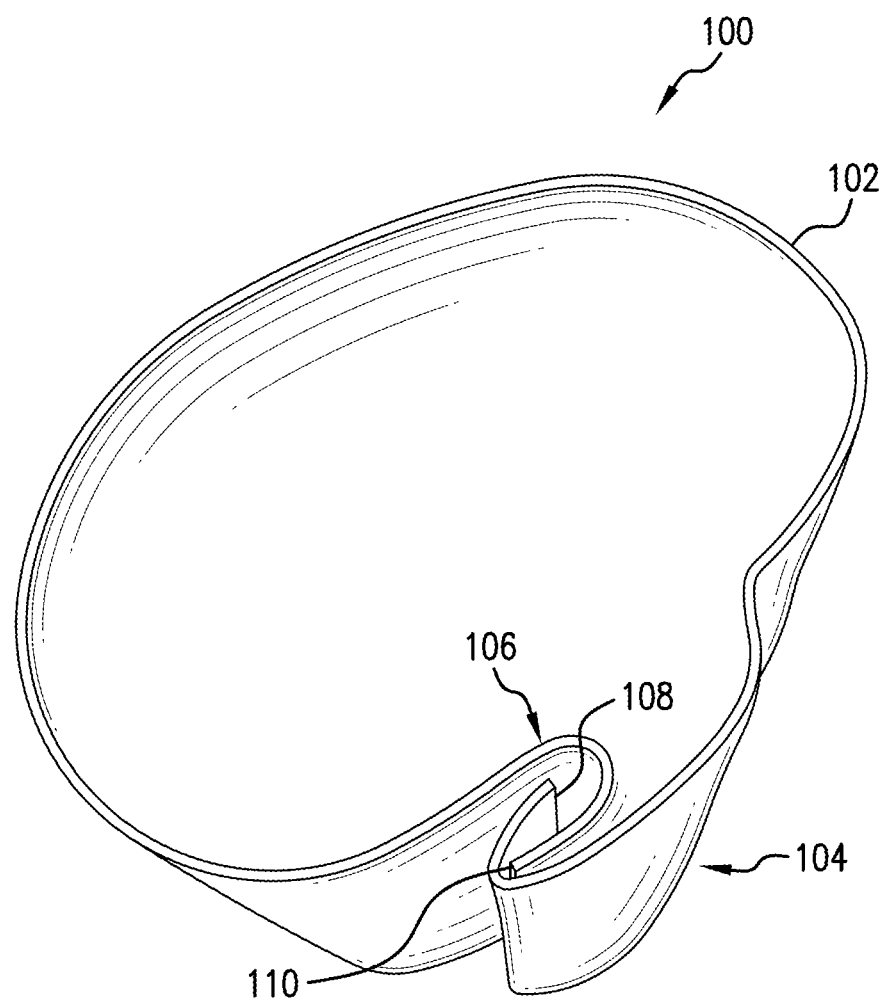
FIG. 8 is a top-perspective view of the cosmetic cover after the cover has been cut to form the latch.

Referring to FIG. 7, clasp 106 is formed from slicing overlapping area of curvature 104 the length of sleeve 102 (represented by dimension E) along a line substantially perpendicular to transverse plane 103. The slice creates a first end 108 and a second end 110 (shown in FIG. 7) represented by the previously joined and continuous overlapping area of curvature 104. Sleeve 102, as shown, is now openable at the slice to separate first end 108 and second end 110 for fitting sleeve 102 around prosthesis 200 and latchable by fitting first end 108 of clasp 106 over second end 110 of clasp 106, as shown in FIG. 8.

Figure 2:
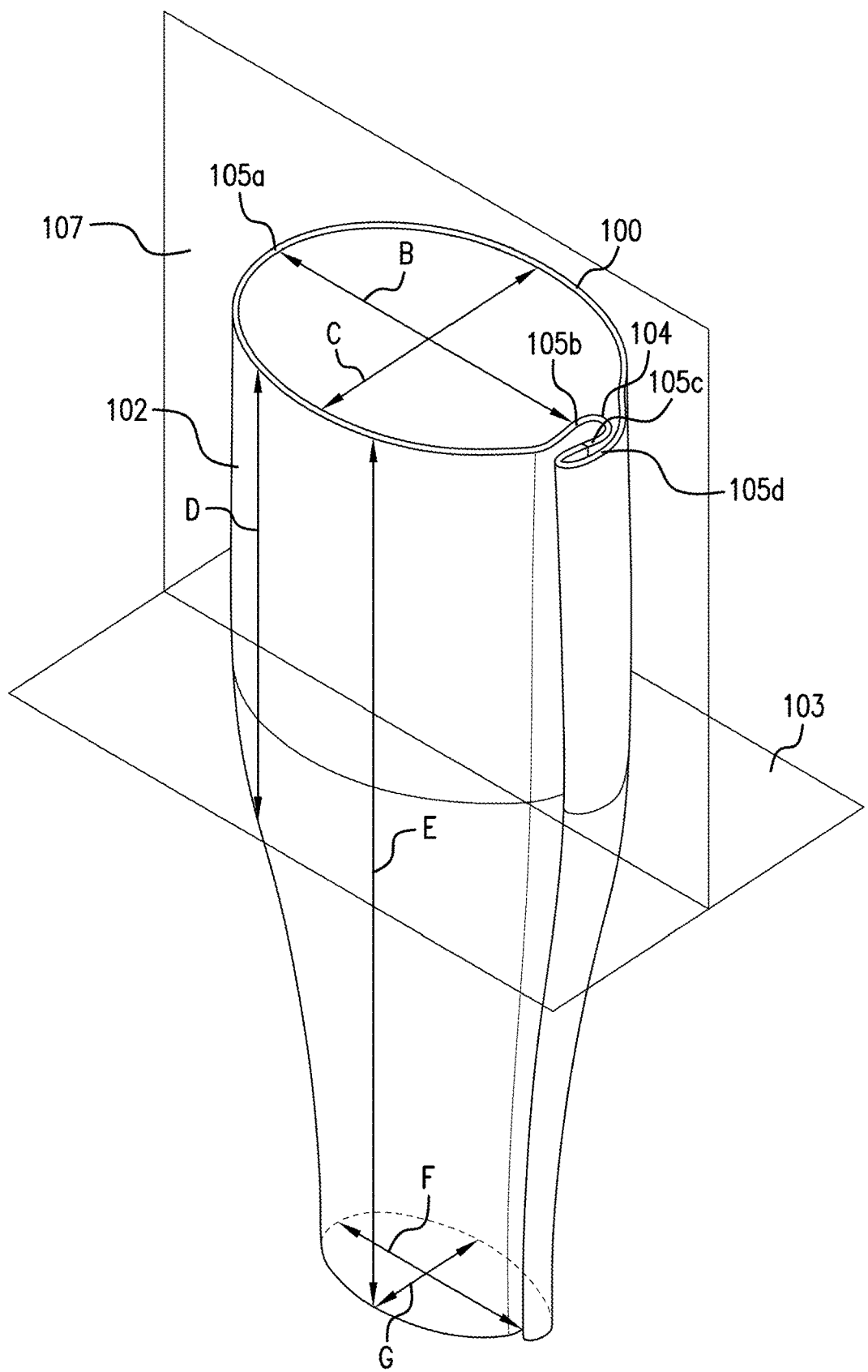
FIG. 2 is a schematic view of the cosmetic cover of FIG. 1 with the important dimensions.
Figure 3:
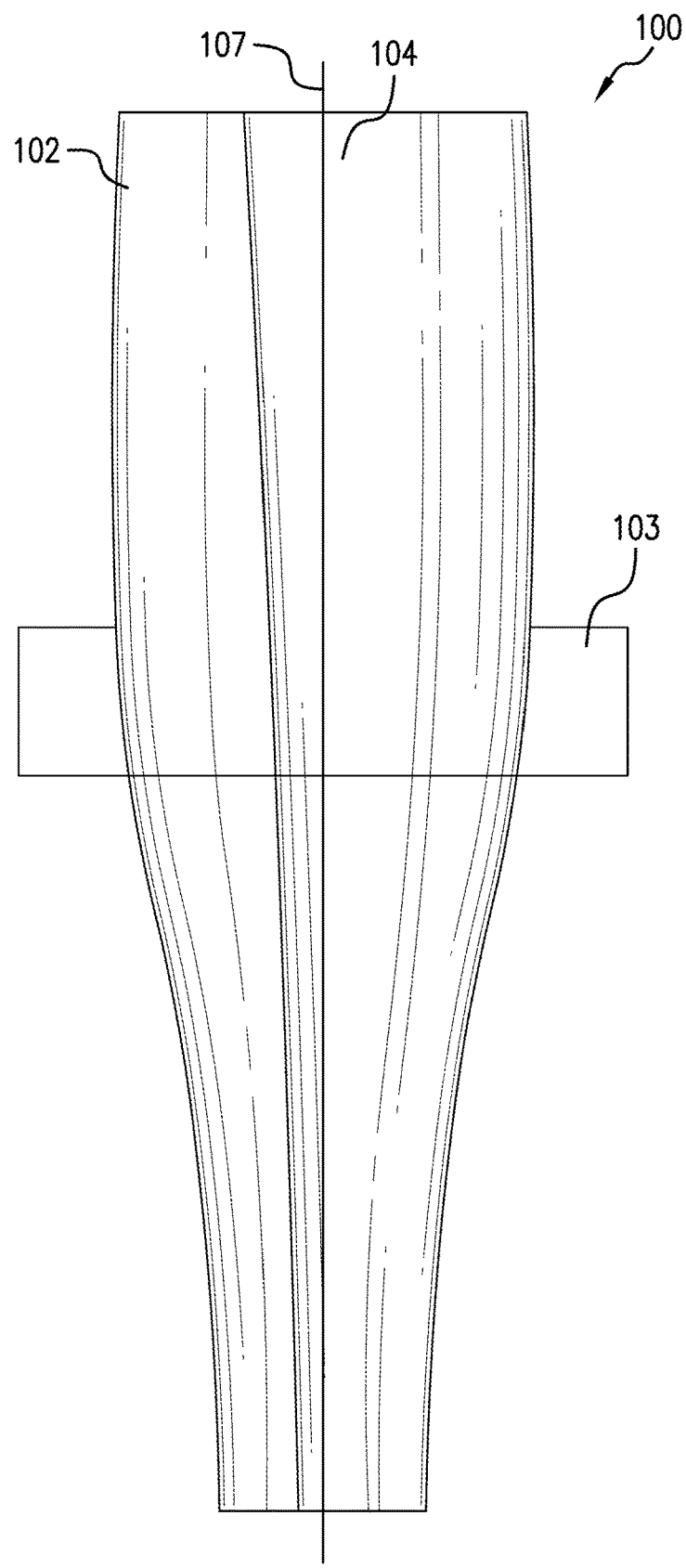
FIG. 3 is a rear view of the cosmetic cover of FIG. 1.
Figure 4:
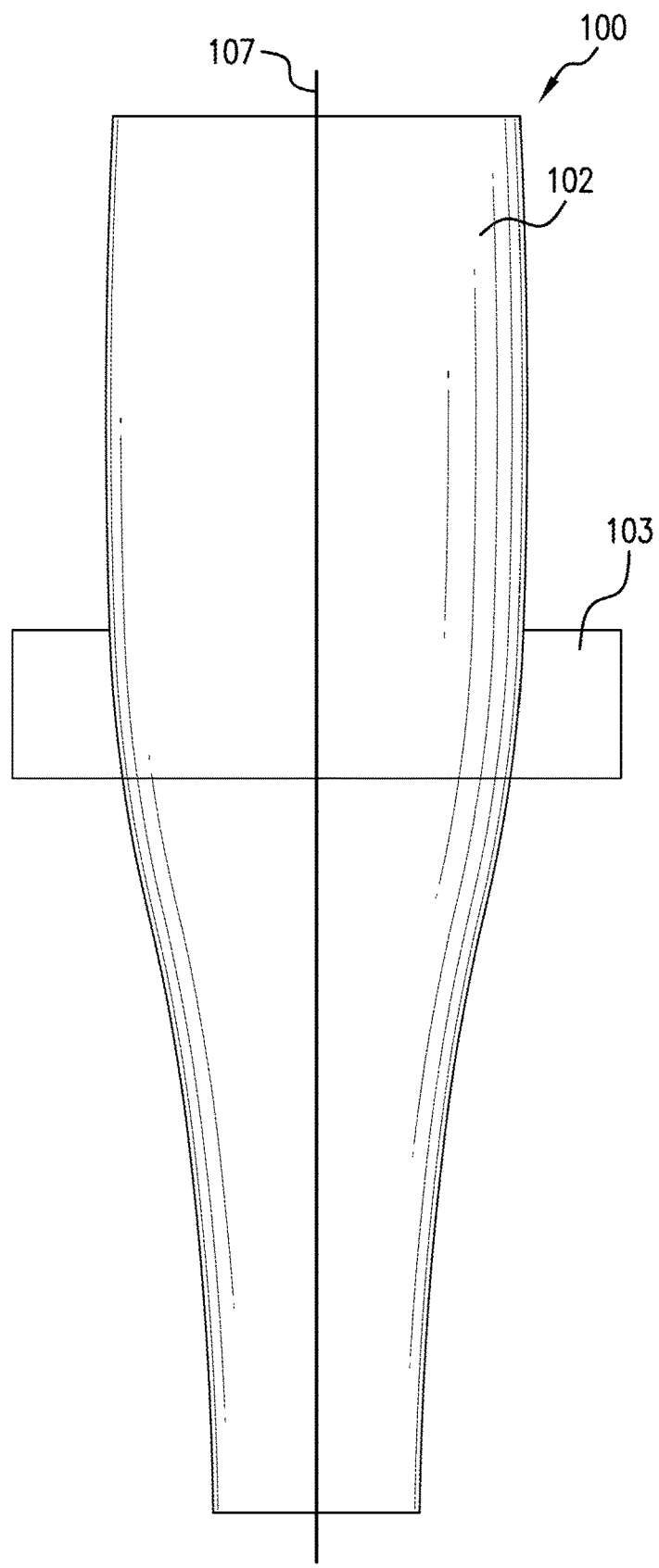
FIG. 4 is a front view of the cosmetic cover of FIG. 1.
Figure 5:
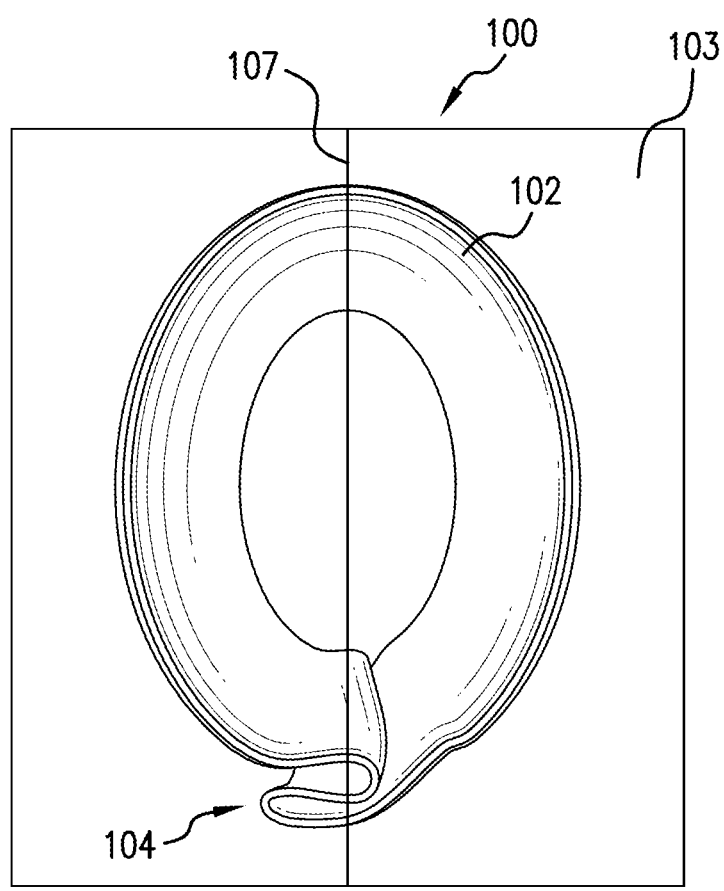
FIG. 5 is a top view of the cosmetic cover of FIG. 1.
Figure 6:
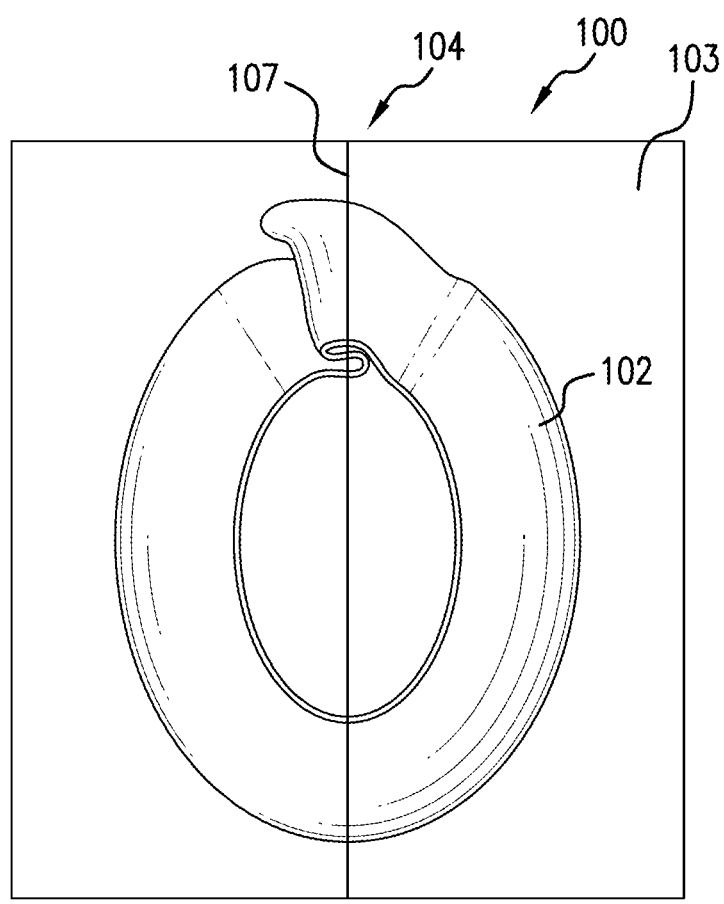
FIG. 6 is a bottom view of the cosmetic cover of FIG. 1.

Prosthesis cover 100 can be tailored to each individual with dimensions B-G for sleeve 102 shown in FIG. 2. Compared to prior art prosthesis, prosthesis cover 100 is designed such that it can be created with a three-dimensional (3D) printer in a continuous operation. As will be described below, the filament nozzle of the 3D printer never has to stop moving. The printing begins at the bottom of the part and continues in a smooth and continuous and uninterrupted path spiraling upward until sleeve 102 is completed. This cuts printing time down by more than thirty-three percent (33%).

Figure 9:
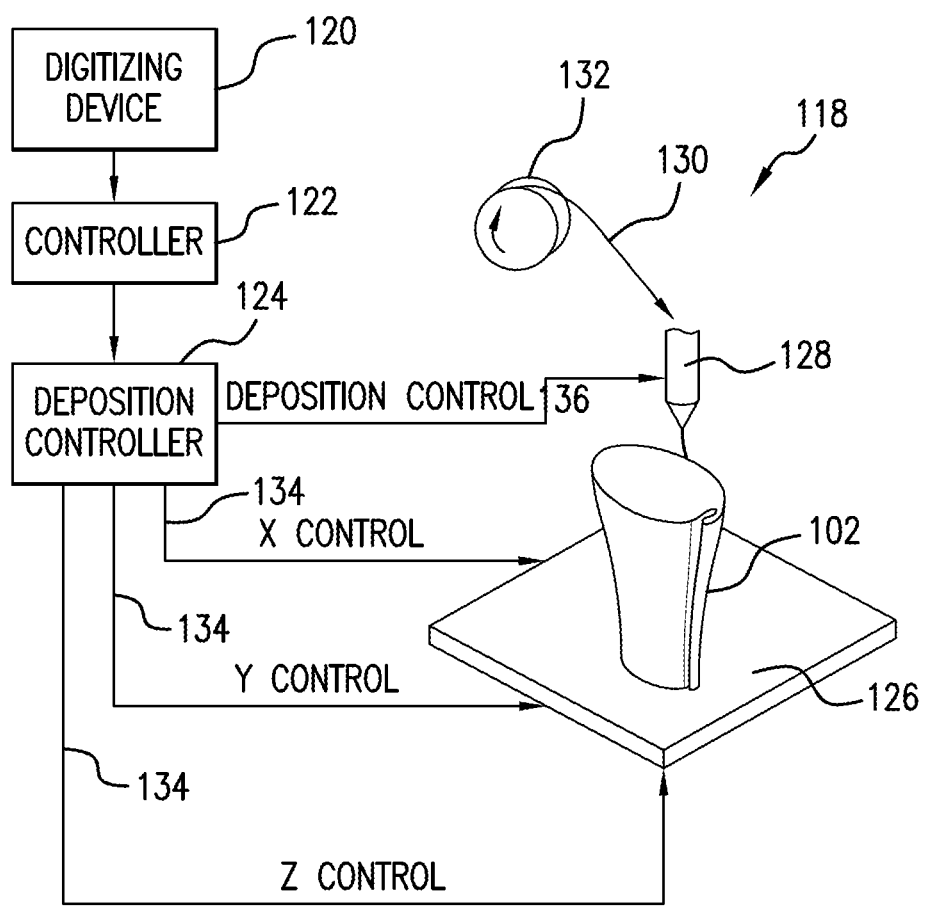
FIG. 9 is a schematic, block-diagram representation of a rapid manufacturing system for use with the present invention

As shown in FIG. 9, the present invention facilitates a completely automated system for fabricating sleeve 102. A 3D printing system 118 is shown in FIG. 9. 3D printing system 118 comprises of a digitizing device 120 that will first create a 3D digital representation (dimensions) of sleeve 102. This digital representation may include the outer surface dimensions B-G shown in FIG. 2 of sleeve 102. These representations can be sent to digitizing device over a network connection from the factory or even direct from the customer. This digital representation will then be fed into a computer aided design ("CAD") system loaded on controller 122, where a knowledge based computer program running on the CAD system will generate the digital dimensions B-G of prosthesis cover 100 to be fabricated based upon the measurements.

Once generated, the dimensions B-G for sleeve 102 are then sent to deposition controller 124 of 3D printing system 118. A suitable 3D printing system 118 for use with the present invention is commercially available from Stratasys, Inc. and uses fused deposition modeling ("FDM") technology. 3D printing system 118 creates three-dimensional objects based upon the digital dimensions supplied by the CAD system on controller 122 by depositing multiple layers of solidifying material, which is initially in a fluid state, onto a platform 126 to build up a three-dimensional sleeve 102 according to the dimensions B-G provided by the CAD system on controller 122. 3D printing system 118 includes a dispensing head 128 for heating and liquefying thermoplastic material 130 supplied by a spool 132, and for depositing the heated liquified material onto platform 126 which moves in the XYZ directions according to instructions 134 sent by deposition controller 124. Deposition controller 124 also sends deposition control instructions 136 to nozzle of dispensing head 128 so as to control the amount and timing of the material deposition. Other 3D printing systems are also known in the art and the present invention is intended for use with these 3D printing systems as well.

During this process the preferred material to provide a prosthesis and a method to fabricate a prosthesis constructed of a material, preferably a thermoplastic material, but other suitable materials may include ULTEM®, carbon fiber, or other material of equal or greater strength that may be known or developed in the future, while the printers are a product of Stratasys Corporation or other such types of printers.

The foregoing describes a method for constructing a prosthesis cover 100 using a 3D printing system 118. This method comprises providing a digital file of a prosthesis cover 100 as described above to digitizing device 120 or sending dimensions to CAD system on controller 122. As previously described, these dimensions can come from digitizing a model of prosthesis cover 100 or sending dimension directly to CAD system on controller 122. The method continues by sending the digital file to 3D printing system 118 where sleeve 102 of prosthesis cover 100 is printed in a continuous motion.

The method continues by printing in the continuous motion sleeve 102 and forming an overlapping area of curvature 104 in sleeve 102 while printing in the continuous motion. In one embodiment, this overlapping area of curvature 104 can be viewed from a cross-section that is parallel to a transverse plane as being intersected at least four times by a perpendicular longitudinal plane extending through overlapping area of curvature 104 in prosthesis cover 100. This is represented in FIG. 2 by an imaginary plane extending from the arrow represented by dimension B to the arrow represented by dimension F. In one embodiment, such overlapping area of curvature 104 is a generally s-shaped curve.

Prosthesis cover 100 can be a generalized model where one or more or all measurements corresponding to dimensions B-G from FIG. 2 are received by CAD system on controller 122 and the method continues by adjusting the digital file based on at least one dimension of dimensions B-G corresponding to the description above.

Once sleeve 102 is fully formed, the method continue by slicing overlapping area of curvature 104 in sleeve 102 along a line substantially perpendicular to the transverse plane for forming clasp 106 from overlapping area of curvature 104 in sleeve 102. By printing sleeve 102 with a suitable material, such a thermoplastic material so that clasp 106 from overlapping area of curvature 104 in sleeve 102 will releasable hold prosthesis cover 100 in a closed position.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

We claim:

1. A prosthesis cover for a prosthesis comprising:
   a sleeve generally shaped as a limb;
   an overlapping area of curvature formed in the sleeve, the overlapping area of curvature formed in a transverse plane that is perpendicular to a longitudinal length of the sleeve wherein the overlapping area of curvature formed in the transverse plane extends the longitudinal length of the sleeve; and a clasp formed from slicing the overlapping area of curvature the length of the sleeve along a line substantially perpendicular to a transverse plane to create a first end and a second end; and the sleeve openable to separate the first end and the second end of the clasp for fitting the sleeve around the prosthesis and latchable by fitting the first end of the clasp over the second end of the clasp.

2. The prosthesis cover of claim 1, wherein the overlapping area of curvature is generally an s-shaped curve.

3. The prosthesis cover of claim 1, wherein the prosthesis cover is intersected by a vertically oriented plane that is perpendicular to a transverse plane at least four times when the vertically oriented plane extends through the overlapping area of curvature in the prosthesis cover.

4. The prosthesis cover of claim 1, wherein the sleeve is made from a thermoplastic material.

5. The prosthesis cover of claim 1, wherein the sleeve is a formed of a single piece of material printed by a 3D printing system in one continuous and uninterrupted motion in a spirally upward motion.

6. A prosthesis cover for a prosthesis comprising:
a sleeve generally shaped as a limb;
an overlapping area of curvature formed in the sleeve, the overlapping area of curvature formed in a transverse plane that is perpendicular to a longitudinal length of the sleeve wherein the overlapping area of curvature formed in the transverse plane extends the longitudinal length of the sleeve; and a clasp formed from slicing the overlapping area of curvature the length of the sleeve along a line substantially perpendicular to a transverse plane to create a first end and a second end; and the sleeve openable to separate the first end and the second end of the clasp for fitting the sleeve around the prosthesis and latchable by fitting the first end of the clasp over the second end of the clasp, wherein the prosthesis cover is intersected by a vertically oriented plane that is perpendicular to a transverse plane at least four times when the vertically oriented plane extends through the overlapping area of curvature in the prosthesis cover.

7. The prosthesis cover of claim 6, wherein the overlapping area of curvature is generally an s-shaped curve.

8. The prosthesis cover of claim 6, wherein the sleeve is made from a thermoplastic material.

9. The prosthesis cover of claim 6, wherein the sleeve is a formed of a single piece of material printed by a 3D printing system in one continuous and uninterrupted motion in a spirally upward motion.

10. The prosthesis cover of claim 9, wherein the sleeve further comprises a major knee dimension, minor knee dimension, top section dimension, total height dimension, major ankle dimension, and minor ankle dimension.

11. A prosthesis cover for a prosthesis comprising:
a sleeve generally shaped as a limb;
an overlapping area of curvature formed in the sleeve, the overlapping area of curvature formed in a transverse plane that is perpendicular to a longitudinal length of the sleeve wherein the overlapping area of curvature formed in the transverse plane extends the longitudinal; and a clasp formed from slicing the overlapping area of curvature the length of the sleeve along a line substantially perpendicular to a transverse plane to create a first end and a second end; and the sleeve openable to separate the first end and the second end of the clasp for fitting the sleeve around the prosthesis and latchable by fitting the first end of the clasp over the second end of the clasp, wherein the sleeve is a formed of a single piece of material printed by a 3D printing system in one continuous and uninterrupted motion in a spirally upward motion.

12. The prosthesis cover of claim 11, wherein the prosthesis cover is intersected by a vertically oriented plane that is perpendicular to a transverse plane at least four times when the vertically oriented plane extends through the overlapping area of curvature in the prosthesis cover.

13. The prosthesis cover of claim 11, wherein the overlapping area of curvature is generally an s-shaped curve.

14. The prosthesis cover of claim 11, wherein the sleeve is made from a thermoplastic material.

15. The prosthesis cover of claim 11, wherein the sleeve further comprises a major knee dimension, minor knee dimension, top section dimension, total height dimension, major ankle dimension, and minor ankle dimension.

\* \* \* \* \*